United States Patent [19]
Weltz et al.

[11] Patent Number: 5,281,823
[45] Date of Patent: Jan. 25, 1994

[54] PHOTOCELL AND QUICK ATTACH CLAMP

[75] Inventors: Richard K. Weltz, Richmond; Peter Schuerch, Mechanicville; James Kallio, Richmond, all of Va.

[73] Assignee: Infilco Degremont, Inc., Richmond, Va.

[21] Appl. No.: 925,386

[22] Filed: Aug. 4, 1992

[51] Int. Cl.$^5$ ............................................. G01J 5/04
[52] U.S. Cl. ................................................ 250/372
[58] Field of Search ...................................... 250/372

[56] References Cited

U.S. PATENT DOCUMENTS

| | | | |
|---|---|---|---|
| 3,062,958 | 11/1962 | Warner | 250/372 |
| 4,017,734 | 4/1977 | Ross | 250/431 |
| 4,061,922 | 12/1977 | Last | 250/461.1 |
| 4,103,167 | 7/1978 | Ellner | 250/432 R |
| 4,272,679 | 6/1981 | Blades | 250/372 |
| 4,467,208 | 8/1984 | Muller et al. | 250/483.1 |
| 4,727,255 | 2/1988 | Monier et al. | 250/352 |
| 4,989,215 | 1/1991 | Winik | 372/70 |

FOREIGN PATENT DOCUMENTS

| | | |
|---|---|---|
| 1429473 | 3/1976 | United Kingdom . |
| 2198530 | 6/1988 | United Kingdom . |
| 9010201 | 9/1990 | World Int. Prop. O. . |

*Primary Examiner*—Constantine Hannaher
*Attorney, Agent, or Firm*—Miller & Christenbury

[57] ABSTRACT

A submersible photocell for detecting ultraviolet light in disinfection apparatus including a quartz jacket capable of transmitting ultraviolet light and a fluorescent material sensitive to ultraviolet light at a wavelength of about 253.7 nm and which produces an infrared secondary emission having a wavelength of about 730–735 nm upon absorption of ultraviolet light. The photocell also includes a photoconductor sensitive to the secondary emission light, is located adjacent the fluorescent material and is capable of varying conductance of electricity upon absorbing light having a wavelength of about 730–735 nm from the infrared secondary emission. The photocell further includes electrically conductive wiring connected to the photoconductor and extending outwardly of the jacket at its remote end. Also, the photocell includes a silicone sponge filler positioned adjacent the photoconductor and around the wiring, together with a nonreactive, non-outgassing ultraviolet light resistant potting compound located adjacent the filler and surrounding the wire to tightly seal the remote end of the jacket from liquids.

19 Claims, 3 Drawing Sheets

PHOTOCELL AND QUICK ATTACH CLAMP

FIELD OF THE INVENTION

The present invention relates to a photocell and a quick attach clamp, particularly to a submersible photocell for detecting ultraviolet light in disinfection apparatus and a quick attach clamp for positioning the photocell at a predetermined alignment and distance from an elongated ultraviolet light source.

BACKGROUND OF THE INVENTION

Systems and apparatus for disinfection of water with ultraviolet light have rapidly developed in view of increased environmental awareness, the accompanying regulation associated with disposal and treatment of waste and potable water and the desire to avoid or reduce reliance on chemical treatment. This growing need has resulted in a similar requirement for producing more efficient and reliable systems for effectively and safely treating waste and potable water over prior art systems.

It is important in achieving this difficult task in ultraviolet treatment systems that all water to be treated, whether passing through an open or closed channel, conduits or the like, is fully treated by exposure to a minimum required quantity of ultraviolet light. Failure of the necessary ultraviolet light dose can result in untreated or improperly treated water and its undesirable consequences. It is accordingly necessary to monitor the ultraviolet light apparatus to insure full coverage of ultraviolet exposure. One means to accomplish this critical task is to directly monitor the intensity of ultraviolet light emanating from one or more ultraviolet light producing lamps utilized in the system. It is important that at least a representative sampling of ultraviolet light intensity be monitored on a continuous basis to ensure that the system provides the necessary dosage of ultraviolet light to the water to be treated.

DESCRIPTION OF THE PRIOR ART

One typical manner in which such monitoring has been attempted is with various types of photocells. However, many of the photocells utilized to date suffer the problem of degradation due to continuous, long term exposure to harmful ultraviolet light. Many photocells and their components utilized in other environments have fared poorly in the severe environment presented by long term exposure to ultraviolet light.

Another disadvantage of many current photocells is that although they are responsive to ultraviolet light, they receive a broad spectrum of light and therefore require optical filters. Such filters are also subject to the degrading effects of ultraviolet light when subjected in a continuous manner. Another problem with filters, as well as lamp jackets, is that they are subject to fouling and distortion as sediments and scum typical of disinfection systems accumulate. A still further problem presents itself in that photocells are submerged during their entire useful life span. This also has caused difficulties in the past due to leakage and corrosion.

Still another disadvantage associated with prior art photocells is the inability to quickly and easily attach and detach the photocell to and from the ultraviolet lamp from which it is measuring ultraviolet light intensity. Prior art devices require cumbersome nut and bolt clamping arrangements that require significant time and effort to attach and detach. Moreover, many of the clamps require attachment to more than one lamp. Also, such attachments require precise measurement and alignment to determine that the photocell is at a predetermined, desired distance and position relative to the lamp.

It is important in taking measurements of ultraviolet light intensity that the photocell remain at a constant distance and in a desired alignment. The typical clamping arrangements require remeasurement, realignment and/or recalibration each time the photocell is moved. Also, a sharp jolt to the lamps or contact by a rigid object can easily shift the photocell position, thereby misaligning the photocell from the ultraviolet light source and destroying its reliability.

OBJECTS OF THE INVENTION

It is an object of the present invention to provide a photocell which is highly resistant to the harmful effects of ultraviolet light, even when subjected to such light over long time periods.

It is another object of the present invention to provide a photocell which is responsive to ultraviolet light without the need for optical filters and that can remain in a submerged condition for long period of time without leakage and/or corrosion.

It is an important object of the invention to provide a photocell having a quickly attachable and detachable clamp for mounting the photocell to a ultraviolet light producing lamp.

It is a further object of the present invention to provide a clamp which maintains the photocell at a constant, predetermined distance from the ultraviolet light source and in a desired alignment configuration, without the need for initial attachment measurements, and which is able to maintain the predetermined distance upon receiving sharp jolts.

Other objects and advantages of the present invention will become apparent to those skilled in the art from the drawings, the detailed description of preferred embodiments and the appended claims.

SUMMARY OF THE INVENTION

The present invention provides a novel submersible photocell for detecting ultraviolet light in disinfection apparatus. The photocell includes a jacket capable of transmitting ultraviolet light and a fluorescent material sensitive to ultraviolet light at a wavelength of about 253.7 nm and which produces an infrared secondary emission having a wavelength of about 730-735 nm upon absorption of ultraviolet light. The photocell also includes a photoconductor sensitive to the secondary emission light, is located adjacent the fluorescent material and is capable of varying its conductance upon absorbing light having a wavelength of about 730-735 nm from the infrared secondary emission. The photocell further includes electrically conductive wiring connected to the photoconductor and extending outwardly of the jacket at its remote end. Also, the photocell includes a silicone sponge filler positioned adjacent the photoconductor and around the wiring, together with a nonreactive, non-outgassing ultraviolet light resistant potting compound located adjacent the filler and surrounding the wire to tightly seal the remote end of the jacket from liquids.

The present invention also provides a quick attach clamp for positioning the photocell at a predetermined distance from an elongated ultraviolet light source and in a desired alignment configuration. The clamp includes a sleeve for housing a portion of the photocell and a potting compound surrounding the portion of the photocell within the sleeve. An epoxy resin plug at the end of the sleeve seals the remote end of the sleeve. A cover is connected to the detection end of the sleeve and has an access opening to the detection end of the photocell. Spaced apart, opposed arms extend from the cover in a direction substantially parallel to an axis running through the center of the opening. Each arm has a portion sized and shaped to firmly grip the outer surface of elongated ultraviolet lamps so that the detection end of the photocell is positioned at a constant, predetermined distance from the light source in a direction and alignment substantially perpendicular to the axis running through the center of the access opening.

DETAILED DESCRIPTION OF THE INVENTION

Figure 1:
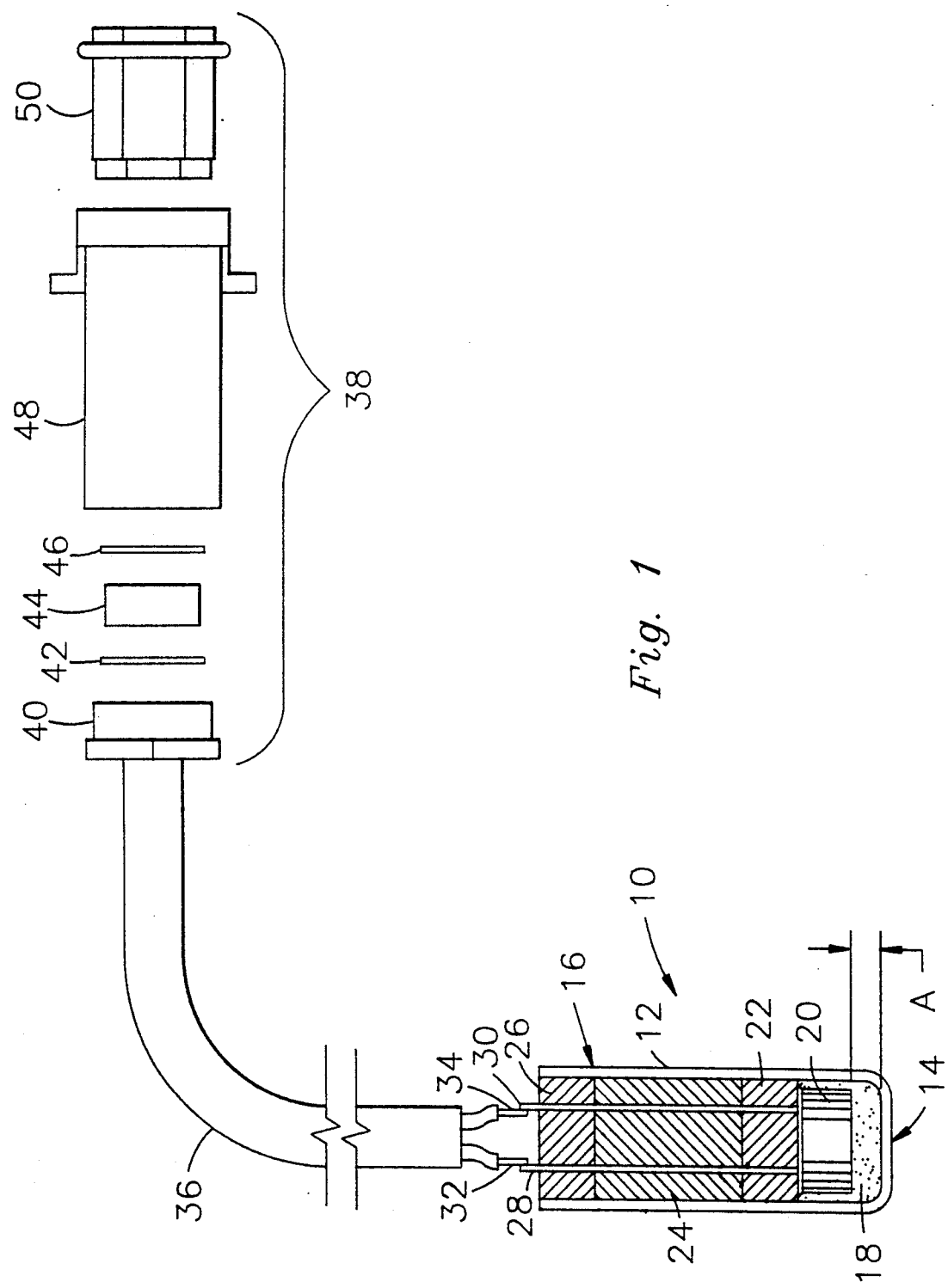
FIG. 1 shows a schematic front elevational view, partially taken in section, of a photocell and connector in accordance with aspects of the invention.

It will be appreciated that the following description is intended to refer to the specific embodiments of the invention selected for illustration in the drawings and is not intended to define or limit the invention, other than in the appended claims.

Turning now to the drawings in general and FIG. 1 in particular, the number 10 designates a photocell in accordance with the invention. Photocell 10 includes and is enclosed by a substantially test-tube shaped quartz jacket 12, which forms the outer surface of the photocell, at least a portion of which is exposed to the surrounding environment. Quartz jacket 10 has a detection end 14 and a remote end 16. The closed detection end 14 of quartz jacket 12 contains fluorescent material 18. Photoconductor 20 is embedded within fluorescent material 18 proximate detection end 14.

First sponge filler 22 is located adjacent photoconductor 20 and contacts fluorescent material 18 at its outermost edges. Potting compound 24 extends from sponge filler 22 toward remote end 16 of jacket 12. Second sponge filler 26 is located at the distal portion of remote end 16 and caps quartz jacket 12.

Electrically conductive wires 28 and 30 connect to photoconductor 20, extend through and are surrounded by first sponge filler 22, extend through and are surrounded by potting compound 24, and extend through and are surrounded by second sponge filler 26. Cable wires 32 and 34 are electrically connected to wires 28 and 30, respectively. In turn, cable wires 32 and 34 extend within and along cable 36. Connector 38 connects to cable 36 and consists of a number of component parts. Proceeding from left to right in FIG. 1, connector 38 includes a sealed end cap 40, washer 42, sealing ring 44, washer 46, connector hood 48 and male insert 50. Connector 38 engages a desired readout means (not shown and well known in the art) such as an intensity meter and its associated connecting wiring, for example.

Figure 2:
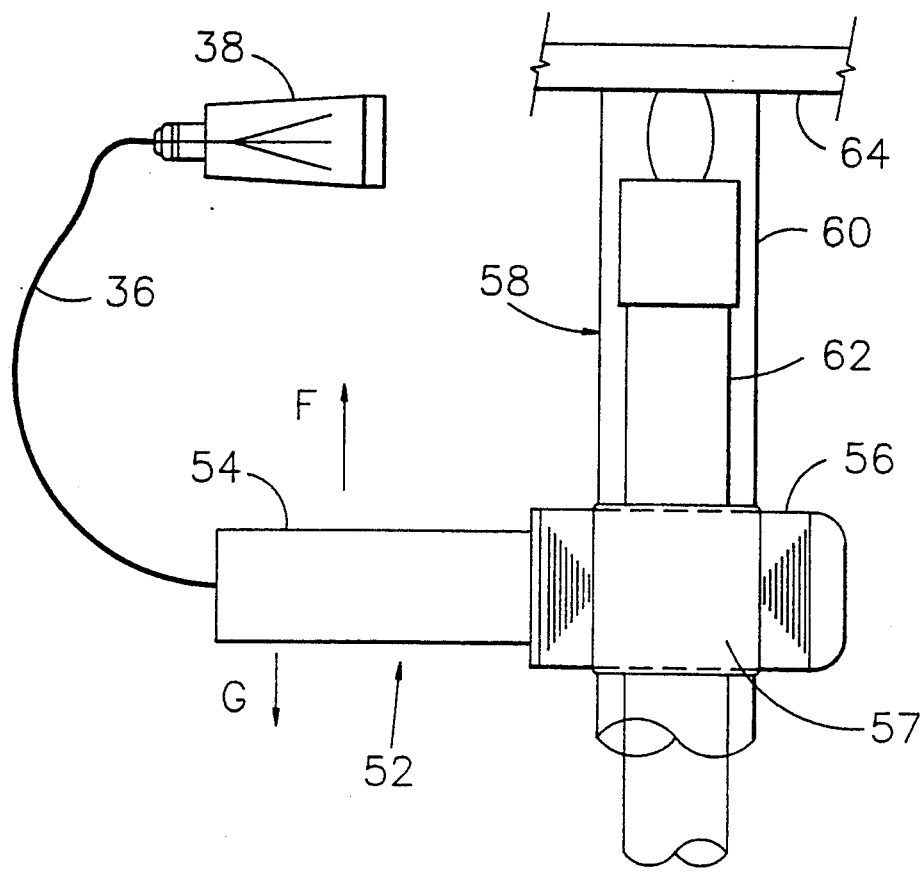
FIG. 2 shows a schematic top plan view of the photocell shown in FIG. 1 placed within a clamp of the invention and attached to an ultraviolet light producing lamp.

FIG. 2 shows clamp 52 of the invention attached to lamp 58. Lamp 58 consists of quartz tube 60, which surrounds ultraviolet light 62 and seals it from surrounding liquids. Clamp 52 includes cable 36 and connector 38 from photocell 10 of FIG. 1, together with sleeve 54 and clamping arm 56. Clamping arm 56 has a rubber sleeve 57 to act as a cushion against lamp 58. Quartz tube 60 and ultraviolet light 62 connect to module frame 64.

Figure 3:
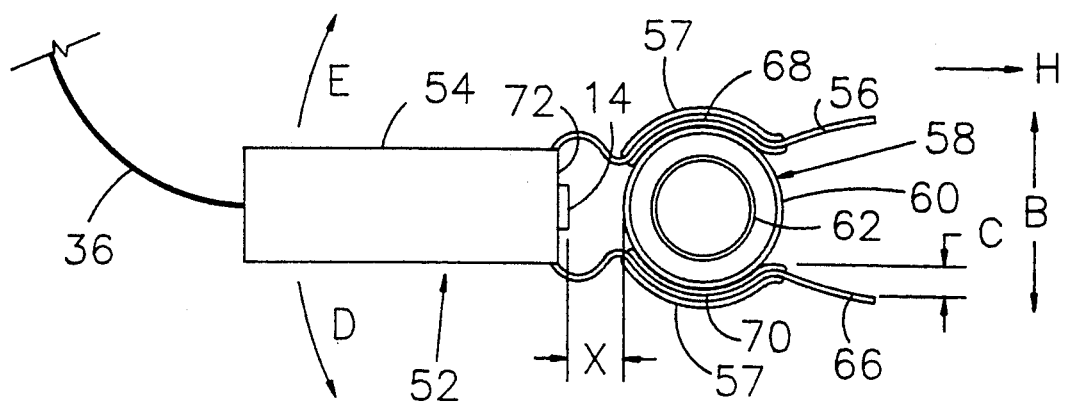
FIG. 3 shows a schematic side view of the photocell and clamp shown in FIG. 2, attached to an ultraviolet light producing lamp, taken in section.

FIG. 3 shows clamp 52 from a side view to better illustrate clamping arm 56 and spaced apart, opposed clamping arm 66. Lamp 58 lies between clamping arms 56 and 66, and in particular, is closely received between curved portions 68 and 70 of clamping arms 56 and 66, respectively. Clamping arm 66 also has a rubber sleeve 67 to act as a cushion against lamp 58. Detection end 14 of photocell 10 extends through cover 72 and lies a predetermined distance "X" from lamp 58.

Figure 4:
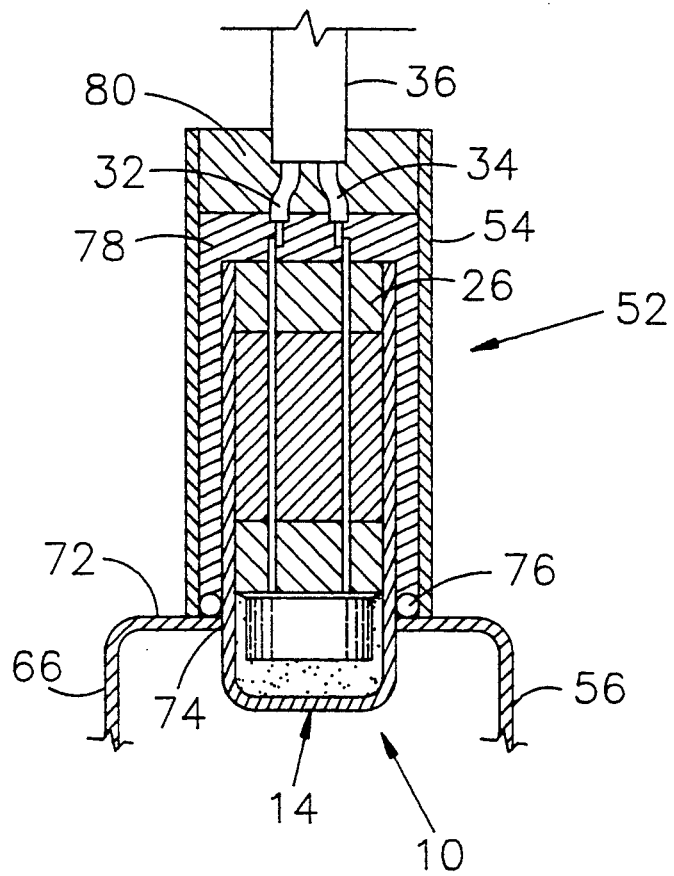
FIG. 4 shows a schematic sectional view of the photocell of FIG. 1 positioned within a sleeve of the clamp shown in FIGS. 2 and 3.

FIG. 4 shows an exploded view of sleeve 54 and photocell 10. Detection end 14 of photocell 10 extends outwardly through access opening 74 in cover 72, which is mounted to one end of sleeve 54. "O" ring 76 is concentrically positioned photocell 10 within sleeve 54. Potting compound 78 surrounds the sealed portion of photocell 10 and extends toward and against "O" ring 76. Resin seal 80 is positioned against potting compound 78 and directly seals against the inner walls of sleeve 54. Potting compound 78 and resin seal 80 surround cable wires 32 and 34, as well as a portion of cable 36. Resin seal 80 seals the remote end of sleeve 54 and provides strain relief for cable 36 and for wires 32 and 34.

Referring now to the drawings generally, the production and use of photocell 10 and clamp 52 will now be described below. Quartz jacket 12 first receives a pre-measured quantity of fluorescent material 18. This is followed by positioning photoconductor 20 against fluorescent material 18 near detection end 14. The thickness of fluorescent material 18 at detection end 14, as represented by the arrows "A" from FIG. 1, is closely determined so that secondary emissions from fluorescent material 18 are within the middle range of sensitivity of photoconductor 20 at a nominal intensity of lamp 58.

In an especially preferred embodiment wherein lithium metaaluminate:iron is employed as fluorescent material 18, and wherein photoconductor 20 is cadmium selenide (CdSe), the thickness "An inch is approximately 3/32" and quartz jacket 12 has a flattened end to maximize photocell sensitivity. Use of a flattened end permits an enlarged 3/32 inch volume of fluorescent material 18 against photoconductor 20.

It is important in assembling photocell 10 that the fluorescent material 18 remain compacted to stabilize its configuration and the resultant photocell output. To assist in maintaining fluorescent material 18 in a compacted condition during assembly, compressible first sponge filler 22 is slid around wires 28 and 30 and downwardly into quartz jacket 12 and against photoconductor 20. First sponge filler 22 is maintained in a compressed condition during introduction of potting compound 24, which follows after introduction of first sponge filler 22. Then, second sponge filler 26 is introduced into quartz jacket 12 to fill out the remaining open space. Cable wires 32 and 34 are then preferably soldered to wires 28 and 30, respectively.

The lithium metaaluminate:iron compound is the especially preferred fluorescent material in photocell 10. The applicants have achieved excellent and unexpected results with Sylvania 232 lithium metaaluminate:iron. However, it is possible that other fluorescent or phosphor materials might be used, so long as they are sensitive to ultraviolet light which has a wavelength of about 253.7 nm. Also, fluorescent material 18 should be capable of emitting secondary emissions in the range of wavelength of about 730-735 nm. Similarly, although cadmium selenide is especially preferred, other photoconductors may be used so long as they are sensitive to infrared light having a wavelength of about 730-735 nm, which matches the secondary emission of the fluorescent material. Type 3 CdSe manufactured by EG&G Vactec has proven to be surprisingly effective.

Sponge fillers 22 and 26 are preferably a closed cell silicone, which is compressible. A number of such silicone sponges are available from General Electric Company and have proven highly advantageous over Neoprene, which tends to degrade when exposed to other components of typical photocells for extended periods of time.

Second sponge filler 26 is preferably introduced into the remote end of quartz jacket 12 in order to maintain wires 26 and 28 in a predetermined, stable position and to seal jacket 12. Use of second sponge filler 26 is preferred since potting compound 24 is typically a gel material having a low bond strength, which upon movement of wires 28 or 30 during installation or maintenance would tend to separate from either or both of wires 28 or 30, thereby potentially reducing the sealing effect of potting compound 24. An especially preferred potting compound 24 which has demonstrated excellent sealing compatibility and longevity is Dow Sylgard 527.

It is critical in selecting fluorescent material 18, photoconductor 20, first sponge filler 22, potting compound 24 and second sponge filler 26 that they all be highly resistant to ultraviolet light and compatible with adjacent materials within photocell 10. Degradation of one or more of these critical components due to long term exposure to ultraviolet light will potentially result in damage or failure of photocell 10. All of the above preferred substances have proven to be extremely compatible and highly resistant to ultraviolet light over long periods of time.

Cover 72 is firmly attached to sleeve 54 by any method known in the art, such as by welding, for example. Cover 72 is preferably integral with clamping arms 56 and 66. Rubber sleeves 57 and 67 are optional and are preferably "shrink" fit polyolefin tubing. Weico Wire & Cable, Inc. produces a number of suitable tubings.

Once photocell 10 is completely assembled, it may be introduced into sleeve 54 of clamp 52 as shown in FIG. 4. This is typically achieved by first sliding "O" ring 76 into sleeve 54 and against cover 72 and then sliding photocell 10 into sleeve 54 so that detection end 14 of photocell 10 extends outwardly through access opening 74 a predetermined distance. "O" ring 76 maintains detection end 14 in a concentric position with respect to sleeve 54 prior to introduction of potting compound 78. Then, potting compound 78 is introduced into sleeve 54 and around the exterior of concentrically located "O" ring 76. Potting compound 78 can be the same or different material from potting compound 24 so long as its ultraviolet resistance and compatibility characteristics are maintained. An epoxy resin seal material 80 is then applied around cable wires 32 and 34 as well as the insulation of cable 36 to tightly seal photocell 10 within sleeve 54.

Photocell 10 and clamp 52 are then ready for attachment to a typical ultraviolet lamp 58. This is performed, by reference to FIG. 3, by simply aligning opposed, spaced apart arms 56 and 66 with lamp 58 and moving arms 56 and 66 toward lamp 58 in the direction shown by arrow "H". The outer surface (or rubber sleeves 57 and 67) of lamp 58 contacts the leading ends of clamping arms 56 and 66, thereby causing them to move apart from one another in the direction shown by arrows "B". Then, lamp 58 lodges itself firmly within the grip of clamping arms 56 and 66 as shown in FIG. 3 by directly matching the radius of curvature of lamp 58 with curved portions 68 and 70. Lamp 58 is retained in position by virtue of the curvative distance of the clamping arms shown between arrows "C".

Once lamp 58 is gripped firmly within its preferred position at curved portion 68 and 70, the outermost surface of lamp 58 is a predetermined distance from detection end 14 of photocell 10. This predetermined distance is represented by arrows "X". This constant, predetermined distance is maintained no matter how and from which direction clamp 52 is attached to lamp 58. Rotation of clamp 52 in the direction of either of arrows "D" or "E" as shown in FIG. 3 results in detection end 14 maintaining the same, constant predetermined distance "X" from lamp 58. The same principle applies even if clamp 52 is slid along lamp 58 in the direction as shown by arrows "F" and "G" in FIG. 2. Also, detection end 14 remains in the same relative alignment position with respect to lamp 58 upon rotation of clamp 52 in the direction of Arrows "D" or "E". These are highly advantageous features of the invention since constant reliable measurement may be taken from any lamp utilized in the system, at any position longitudinally along the lamp or in any position rotationally around the lamp.

Although this invention has been described in connection with specific forms thereof, it will be appreciated that a wide variety of equivalents may be substituted for the specific elements shown and described herein without departing from the spirit and scope of this invention as described in the appended claims.

We claim:

1. An optical filter free photocell for detecting ultraviolet light comprising:
   a sealed, water tight jacket capable of transmitting ultraviolet light, said jacket having a detection end;
   an ultraviolet light sensitive fluorescent material located adjacent said detection end and producing a secondary emission in response to said ultraviolet light;
   a photoconductor located adjacent said fluorescent material and inwardly of said jacket capable of varying conductance of electricity upon absorbing said secondary emission; and
   members connected to said photoconductor and extending outwardly of said jacket to transmit the degree of conductance variation.

2. The photocell defined in claim 1 wherein said fluorescent material comprises lithium metaaluminate:iron.

3. The photocell defined in claim 1 wherein said fluorescent material is sensitive to light having a wavelength of about 253.7 nm.

4. The photocell defined in claim 1 wherein said secondary emission is infrared light.

5. The photocell defined in claim 1 wherein said secondary emission has a wavelength of about 730-735 nm.

6. The photocell defined in claim 1 wherein said photoconductor comprises cadmium selenide.

7. The photocell defined in claim 1 wherein said photoconductor is sensitive to light having a wavelength of about 735 nm.

8. The photocell defined in claim 1 wherein said jacket is made from quartz.

9. The photocell defined in claim 1 further comprising an ultraviolet light resistant sealant adjacent said photoconductor to tightly seal said jacket.

10. The photocell defined in claim 9 wherein said sealant is non-reactive and non-outgassing.

11. The photocell defined in claim 9 wherein said sealant comprises:
   a compressible silicone sponge filler positioned adjacent said photoconductor and around said members; and
   a potting compound positioned adjacent said sponge and around said members.

12. The photocell defined in claim 11 further comprising a non-reactive ultraviolet light resistant sponge filler positioned adjacent said potting compound.

13. The photocell defined in claim 1 wherein said members are electrically conductive.

14. The photocell defined in claim 1 further comprising supplemental sealing means which comprise:
   a sleeve positioned around at least a portion of said jacket away from said detection end;
   a potting compound within said sleeve and surrounding at least a portion of the jacket away from said detection end; and
   an epoxy resin plug positioned in an end of said sleeve opposite said detection end.

15. The photocell defined in claim 14 wherein said potting compound surrounds said members extending outwardly from said jacket.

16. An optical filter free submersible photocell for detecting ultraviolet light in disinfection apparatus comprising:
   a quartz jacket capable of transmitting ultraviolet light without undue attenuation, said jacket having a detection end;
   a fluorescent material sensitive to ultraviolet light at a wavelength of about 253.7 nm located adjacent said detection end and producing an infrared secondary emission having a wavelength of about 730-735 nm upon absorption of said ultraviolet light;
   a photoconductor sensitive to light having a wavelength of about 730-735 nm and located adjacent said fluorescent material and capable of varying conductance upon absorbing light having a wavelength of about 730-735 nm from said infrared secondary emission;
   electrically conductive members connected to said photoconductor and extending outwardly of said jacket;
   a non-reactive, ultraviolet light resistant silicone sponge filler positioned adjacent said photoconductor and around said members; and
   a non-reactive, non-outgassing ultraviolet light resistant potting compound adjacent said filler and surrounding said members to tightly seal said jacket.

17. The photocell defined in claim 16 wherein said fluorescent material comprises lithium metaaluminate:iron.

18. The photocell defined in claim 16 wherein said photoconductor comprises cadmium selenide.

19. The photocell defined in claim 16 wherein said filler is compressible to maintain said fluorescent material in a tightly packed condition.

* * * * *